(12) United States Patent
Galperin et al.

(10) Patent No.: US 7,407,907 B2
(45) Date of Patent: *Aug. 5, 2008

(54) DUAL FUNCTIONAL CATALYST FOR SELECTIVE OPENING OF CYCLIC PARAFFINS AND PROCESS FOR USING THE CATALYST

(75) Inventors: Leonid B. Galperin, deceased, late of Wilmette IL (US); Irina Galperin, legal representative, Wilmette, IL (US); Michael J. McCall, Geneva, IL (US); Joseph A. Kocal, Glenview, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/467,189

(22) Filed: Aug. 25, 2006

(65) Prior Publication Data

US 2006/0281628 A1 Dec. 14, 2006

Related U.S. Application Data

(63) Continuation-in-part of application No. 10/705,793, filed on Nov. 7, 2003, now abandoned.

(51) Int. Cl.
| | |
|---|---|
| C01B 33/36 | (2006.01) |
| C01B 39/00 | (2006.01) |
| C01F 7/00 | (2006.01) |
| B01J 29/06 | (2006.01) |
| B01J 21/00 | (2006.01) |
| B01J 29/00 | (2006.01) |
| B01J 27/182 | (2006.01) |

(52) U.S. Cl. ............... 502/64; 502/65; 502/66; 502/73; 502/74; 502/214; 423/700

(58) Field of Classification Search ............ 502/64–66, 502/73, 74, 214; 423/700, DIG. 30
See application file for complete search history.

(56) References Cited

U.S. PATENT DOCUMENTS

| | | | | |
|---|---|---|---|---|
| 3,617,511 | A | 11/1971 | Jenkins et al. | 208/112 |
| 4,859,312 | A * | 8/1989 | Miller | 208/111.3 |
| 5,345,026 | A | 9/1994 | Chang et al. | 585/700 |
| 5,382,730 | A | 1/1995 | Breckenridge et al. | 585/310 |
| 5,463,155 | A | 10/1995 | Galperin et al. | 585/310 |
| 5,811,624 | A | 9/1998 | Hantzer et al. | 585/700 |
| 5,898,090 | A * | 4/1999 | Hammerman et al. | 585/477 |
| 6,204,426 | B1 | 3/2001 | Miller et al. | 585/739 |
| 6,235,962 | B1 | 5/2001 | Zeuthen | 585/940 |
| 6,241,876 | B1 | 6/2001 | Tsao et al. | 208/137 |
| 6,458,265 | B1 | 10/2002 | Miller et al. | 208/137 |
| 6,566,569 | B1 | 5/2003 | Chen et al. | 585/324 |
| 6,586,650 | B2 | 7/2003 | Baird, Jr. et al. | 585/737 |
| 6,623,625 | B2 | 9/2003 | Baird, Jr. et al. | 208/137 |
| 6,723,889 | B2 | 4/2004 | Miller et al. | 585/739 |
| 6,752,980 | B1 * | 6/2004 | Moscoso et al. | 423/718 |
| 6,756,030 | B1 * | 6/2004 | Jan et al. | 423/718 |
| 6,890,511 | B2 * | 5/2005 | Rohde et al. | 423/705 |
| 7,091,390 | B2 * | 8/2006 | Jan et al. | 585/467 |
| 2001/0006155 | A1 | 7/2001 | Miller et al. | 208/18 |
| 2002/0040175 | A1 | 4/2002 | Baird, Jr. et al | 585/700 |
| 2002/0043481 | A1 | 4/2002 | Baird, Jr. et al. | 208/137 |
| 2004/0015811 | A1 | 1/2004 | Freitas et al. | 717/100 |
| 2004/0182744 | A1* | 9/2004 | Jan et al. | 208/111.01 |
| 2004/0199036 | A1 | 10/2004 | Jan et al. | 585/467 |
| 2006/0281957 | A1* | 12/2006 | Galperin et al. | 585/353 |

* cited by examiner

*Primary Examiner*—J. A. Lorengo
*Assistant Examiner*—Patricia L Hailey
(74) *Attorney, Agent, or Firm*—Frank S Molinaro

(57) ABSTRACT

A catalyst for selectively opening cyclic paraffins has been developed. The catalyst comprises a Group VIII metal, such as platinum, a modifier component, such as niobium or ytterbium, a molecular sieve, such as UZM-16 and a refractory inorganic oxide such as alumina. The Group VIII metal and modifier component are preferably deposited on the refractory inorganic oxide. A process for using the catalyst is also disclosed.

12 Claims, No Drawings

US 7,407,907 B2

DUAL FUNCTIONAL CATALYST FOR SELECTIVE OPENING OF CYCLIC PARAFFINS AND PROCESS FOR USING THE CATALYST

CROSS-REFERENCE TO RELATED APPLICATION

This application is a Continuation-In-Part of application Ser. No. 10/705,793, filed Nov. 7, 2003, now abandoned, the contents of which are hereby incorporated by reference in their entirety.

FIELD OF THE INVENTION

This invention relates to a catalyst for the selective opening of cyclic paraffins which comprises a Group VIII metal component, a modifier component, a molecular sieve and a refractory oxide. This invention also relates to a process for selective ring opening using the catalyst.

BACKGROUND OF THE INVENTION

Olefins are used in various reactions to produce important chemical compounds. Accordingly, demand for olefins is ever increasing and therefore new processes or increased efficiencies in existing processes are required. One of the main processes used in preparing light olefins is naphtha steam cracking. It is known that the efficiency of steam cracking depends on the specific composition of the naphtha feed. Specifically it has been demonstrated that converting naphthenes to acyclic paraffins, e.g. n-paraffins significantly improves olefin yield from the steam cracker. There is, therefore, a need for an improved ring opening catalyst.

Improved ring opening catalysts are also necessary because of increasing demand for environmentally friendly products and clean burning high performance fuels. In this case naphthene rings are opened to give acyclic paraffins which in turn can be isomerized. These isomerized paraffins have improved characteristics than the corresponding naphthenes.

An increased amount of paraffins is also required in providing reformulated gasoline. Reformulated gasoline differs from the traditional product in having a lower vapor pressure, lower final boiling point, increased content of oxygenates, and lower content of olefins, benzene and aromatics.

Reduction in gasoline benzene content often has been addressed by changing the cut point between light and heavy naphtha, directing more of the potential benzene formers to isomerization instead of to reforming. No benzene is formed in isomerization, wherein benzene is converted to $C_6$ naphthenes and $C_6$ naphthenes are isomerized toward an equilibrium mixture of cyclohexane and methylcyclopentane or converted to paraffins through ring opening. It is believed that such $C_6$ cyclics are preferentially adsorbed on catalyst sites relative to paraffins, and the cyclics thus have a significant effect on catalyst activity for isomerization of paraffins. Refiners thus face the problem of maintaining the performance of light-naphtha isomerization units which process an increased concentration of feedstock cyclics.

Catalysts which are useful for ring opening are known and include a high chloride platinum component dispersed on a refractory inorganic oxide which is described in U.S. Pat. No. 5,463,155. U.S. Pat. No. 5,811,624 describes a catalyst for the selective opening of 5 and 6 membered rings which consists of a transition metal catalyst selected from the group consisting of carbides, nitrides, oxycarbides, oxynitrides, and oxycarbonitrides. The transition metal is selected from the group consisting of metals from Group IVA, VA, VIA of the Periodic Table of the Elements. U.S. Pat. No. 6,235,962 B1 discloses a catalyst for ring opening which comprises a carrier consisting of alumina, a metal modifier selected from the group consisting of scandium, yttrium and lanthanum, and at least one catalytically active metal selected from the group consisting of platinum, palladium, rhodium, rhenium, iridium, ruthenium, and cobalt. U.S. Pat. No. 5,382,730 discloses a process for ring opening and isomerization of hydrocarbons where the catalyst comprises an aluminosilicate zeolite such as Zeolite Y or Zeolite Beta and a hydrogenation component. U.S. Pat. No. 5,345,026 discloses a process for conversion of cyclic hydrocarbons to non-cyclic paraffin hydrocarbons where the catalyst comprises a hydrogenation-dehydrogenation component and an acidic solid component comprising a group IVB metal oxide modified with an oxyanion of a group VIB metal. U.S. Pat. No. 3,617,511 discloses a catalyst for conversion of cyclic hydrocarbons to paraffins where the catalyst comprises rhodium or ruthenium on a halogen promoted refractory oxide. U.S. Pat. No. 6,241,876 discloses a ring opening catalyst which comprises a large pore crystalline molecular sieve component with a faujasite structure and an alpha acidity of less than one and a Group VIII noble metal. U.S. Publication No. 2002/43481 A1 discloses a catalyst for naphthalene ring opening which comprises at least one Group VIII metal selected from iridium, platinum, rhodium and ruthenium on a refractory inorganic oxide substrate containing at least one of an alkali metal and alkaline earth metal. Finally U.S. Publication No. 2002/40175 A1 discloses a naphthene ring opening catalyst comprising a Group VIII metal selected from iridium, platinum, palladium, rhodium, ruthenium and combinations thereof. With the metal being supported on the substrate comprising at least one of a Group IB, IIB, and IVA metal.

Applicants have developed an improved catalyst which takes cyclic paraffins such as methylcyclohexane and converts them to normal or branched paraffins of substantially the same carbon number. The catalyst comprises a Group VIII (IUPAC 8-10) metal component, a molecular sieve, a modifier component and a refractory inorganic oxide. The molecular sieves include those having 8, 10 or 12 ring pores and which promote minimal or no cracking, while preferred Group VIII metals include platinum and palladium and modifiers include niobium and titanium.

SUMMARY OF THE INVENTION

As stated, this invention relates to a catalyst for opening naphthenic (paraffinic) rings to produce acyclic paraffins with substantially the same carbon number. Accordingly, one embodiment of the invention is a catalyst for opening cyclic paraffins comprising a Group VIII (IUPAC Groups 8-10) metal component, a modifier component, a molecular sieve and a refractory inorganic oxide, the molecular sieve characterized in that it has an OH peak shift in its CO-FTIR spectrum of less than 310 $cm^{-1}$.

Another embodiment of the invention is a process for producing acyclic paraffins from cyclic paraffins comprising contacting a feed stream comprising cyclic paraffins with a catalyst comprising a Group VIII (IUPAC 8-10) metal component, a modifier component, a molecular sieve and a refractory inorganic oxide at ring opening conditions to convert at least a portion of the cyclic paraffins to acyclic paraffins, and the molecular sieve characterized in that it has an OH peak shift in its CO-FTIR spectrum of less than 310 $cm^{-1}$.

These and other objects and embodiments will become clearer after a detailed description of the invention.

DETAILED DESCRIPTION OF THE INVENTION

One aspect of the present invention is a catalyst which is useful for opening or cleaving naphthenic rings. Ring opening as used herein refers to the breaking of one C—C bond in the ring without any further C—C bond breaks. The further breaking of C—C bonds is commonly referred to as cracking and is specifically excluded from the definition of ring opening. Accordingly, the major product of a ring opening reaction is an acyclic, e.g. normal or branched, paraffin having substantially the same, or higher, molecular weight or the same number of carbon atoms as the starting cyclic paraffin or naphthene. The molecular weight of the product will often be higher through the addition of a hydrogen.

In order to carry out such a reaction, the catalyst of the present invention comprises a catalytic Group VIII metal component, a modifier component, a molecular sieve and a refractory inorganic oxide. The function of the Group VIII metal component is to catalyze the C—C bond break, while the molecular sieve's function is to isomerize cyclohexane rings, both substituted and unsubstituted to cyclopentane rings. The refractory inorganic oxide can act as a support for the catalytic metal component and act as a binder when forming the catalyst into a shaped article. As will be shown later in detail, the Group VIII metal component can also be deposited on the molecular sieve or a combination of refractory inorganic oxide and molecular sieve.

The molecular sieves which can be used in the present invention are any of those which have 8, 10 or 12 ring pores and which have weak to medium acidity. Acidity of the molecular sieves can be determined by one of several techniques. One way to determine the acidity of a molecular sieve is to use Fourier Transform Infra Red (FTIR) Spectroscopy, specifically carbon monoxide (CO-FTIR) spectroscopy. Carbon monoxide, when adsorbed at liquid nitrogen temperatures, has been shown to be a suitable probe for measuring relative strengths of Brönsted acid sites in molecular sieve samples. CO forms H-bonded complexes with hydroxyl groups that are easily detected is by infrared spectroscopy in both the O—H and C—O stretching regions. When CO adsorbs on a hydroxyl group at liquid nitrogen temperatures, the O—H bond is strongly perturbed and the stretching band is broadened and shifted to lower frequency. The magnitude of this shift is proportional to the strength of the acidic proton. It has been found that molecular sieves with an OH peak shift with CO addition of less than 310 cm$^{-1}$ and preferably less than 270 cm$^{-1}$ produce the greatest amount of paraffins with the same number of carbon atoms as the starting naphthenes, i.e. minimal or no cracking.

Another method of measuring acidity is to measure the ability of the molecular sieves to crack heptane, i.e. heptane cracking test. The cracking test involves placing a sample (about 250 mg) of the molecular sieve to be tested into a microreactor and drying the catalyst for 30 minutes at 200° C. using flowing hydrogen. The sample is then reduced by heating for one hour at 500° C. in flowing hydrogen. After cooling to 450° C. a feedstream comprising hydrogen gas saturated with heptane at 0° C. is flowed over the sample resulting in a WHSV of 3.5-4.0 h$^{-1}$. Online analysis of the effluent gas is carried out using gas chromatography after holding for 20 minutes at a temperature from 450-550° C. A weakly acidic molecular sieve will have a heptane conversation of no more that about 20% and preferably no more than about 10%, while a moderately acidic molecular sieve will have a cracking conversion of no more than about 40% and preferably no more than about 30%. Another test method is ammonia temperature programmed desorption or NH$_3$-TPD. Here the sample is saturated with ammonia and the ammonia is desorbed over a temperature range of about 200° C. to about 500° C. The amount of ammonia adsorbed vs the desorption temperature indicates the relative number and strength of the acid sites. Details of this test procedure are provided in U.S. Pat. No. 4,894,142 which is incorporated herein by reference. Molecular sieves with moderate acidity will desorb less than about 0.4 mmol of NH$_3$/g total over the 200° C. to 500° C. range, while a weakly acidic molecular sieve will desorb a total of less than 0.2 mmol of NH$_3$/g over the 200° C. to 500° C. temperature range. Finally, acidity can be measured by pyridine infrared (IR). Specific examples of molecular sieves with weak to moderate acidity, include but are not limited to MAPSOs, SAPOs, UZM-4, UZM-4M, UZM-5, UZM-5P, UZM-5HS, UZM-6, UZM-8, UZM-8HS, UZM-15, UZM-15HS, UZM-16, UZM-16HS and mixtures thereof. Of course it is understood that only those MAPSOs and SAPOs included within the scope of the invention are those that meet the above acidity criteria. Specific SAPOs included in the scope of the invention are SAPO-11, SM-3 and SAPO-34.

MAPSO molecular sieves are disclosed in U.S. Pat. No. 4,758,419 which is incorporated by reference in its entirety. A preferred MAPSO is MAPSO-31. SAPO molecular sieves are disclosed in U.S. Pat. No. 4,440,871 which is incorporated by reference in its entirety. Preferred SAPOs are SAPO-11, SAPO-34 and SM-3 (U.S. Pat. No. 4,943,424 which is incorporated by reference in its entirety). UZM-4 is described in U.S. Pat. No. 6,419,895 B1 while UZM-5, UZM-5P and UZM-6 are described in U.S. Pat. No. 6,388,157 B1 both of which are incorporated in their entirety by reference. The other UZM zeolites are described in the following U.S. patents or patent applications.

| Zeolite | U.S. Application No. | U.S. Pat. No. |
| --- | --- | --- |
| UZM-4M | 10/142,806 | 6,776,975 |
| UZM-5HS | 10/251,590 | 6,982,074 |
| UZM-8 | 10/395,466 | 6,756,030 |
| UZM-8HS | 10/395,624 | — |
| UZM-15 and UZM-15HS | 10/395,399 | 6,890,511 |
| UZM-16 and UZM-16HS | 10/395,639 | 6,752,980 |

All of these U.S. patent applications are incorporated in their entirety by reference. Further, all the molecular sieves identified by a UZM designation will collectively be referred to as UZM zeolites. For completeness, the following brief description of the UZM zeolites described in the patent applications above will be provided below.

All of the UZM zeolites have a microporous crystalline structure of at least AlO$_2$ and SiO$_2$ tetrahedral units. UZM-8, UZM-15 and UZM-16 have a composition on an as-synthesized and anhydrous basis expressed by an empirical formula of:

$$M_m^{n+}R_r^{p+}Al_{1-x}E_xSi_yO_z \qquad (1).$$

M is at least one exchangeable cation selected from the group consisting of alkali and alkaline earth metals, "m" is the mole ratio of M to (Al+E) and, "n" is the weighted average valence of M. R is defined as follows:

1) UZM-8: R is at least one organoammonium cation selected from the group consisting of quaternary ammonium cations, diquaternary ammonium cations, protonated amines, protonated diamines, protonated alkanolamines and quaternized alkanolammonium cations, "r" is the mole ratio of R to (Al+E).
2) UZM-15: R is at least one first quaternary organoammonium cation comprising at least one organic group having at least two carbon atoms, and optionally a second organoammonium cation selected from the group consisting of quaternary ammonium cations, protonated amines, protonated diamines, protonated alkanolamines, diquaternaryammonium cations, quaternized alkanolamines and mixtures thereof, "r" is the mole ratio of R to (Al+E); and
3) UZM-16: R is benzyltrimethylammonium (BzTMA) cation or a combination of BzTMA and at least one organoammonium cation selected from the group consisting of quaternary ammonium cations, protonated amines, protonated diamines, protonated alkanolamines, diquaternaryammonium cations, quaternized alkanolamines and mixtures thereof, "r" is the mole ratio of R to (Al+E).

E is an element selected from the group consisting of Ga, Fe, In, Cr, B, and mixtures thereof. The other variables are defined as "p" is the weighted average valence of R; "x" is the mole fraction of E, "y" is the mole ratio of Si to (Al+E) and "z" is the mole ratio of O to (Al+E). The values of "m", "n", "r", "p", "x", "y" and "z" are presented in Table A.

TABLE A

| Variable | UZM-8 | UZM-15 | UZM-16 |
|---|---|---|---|
| m | 0 to about 2.0 | 0 to about 2.0 | 0 to about 0.75 |
| n | about 1 to about 2 | about 1 to about 2 | about 1 to about 2 |
| r | about 0.05 to about 5.0 | about 0.25 to about 5.0 | about 0.25 to about 5.0 |
| p | about 1 to about 2 | about 1 to about 2 | about 1 to about 2 |
| x | 0 to about 1.0 | 0 to about 1.0 | 0 to about 1.0 |
| y | about 6.5 to about 35 | about 7 to about 50 | about 3 to about 2.5 |
| z | $(m \cdot n + r \cdot p + 3 + 4 \cdot y)/2$ | $(m \cdot n + r \cdot p + 3 + 4 \cdot y)/2$ | $(m \cdot n + r \cdot p + 3 + 4 \cdot y)/2$ |

These zeolites are also characterized by x-ray diffraction patterns having at least the d-spacings and relative intensities set forth in Table B (UZM-8), Table C (UZM-15) and Table D (UZM-16).

TABLE B (UZM-8)

| 2-θ | d(Å) | $I/I_0$ % |
|---|---|---|
| 6.40-6.90 | 13.80-12.80 | w-s |
| 6.95-7.42 | 12.70-11.90 | m-s |
| 8.33-9.11 | 10.60-9.70 | w-vs |
| 19.62-20.49 | 4.52-4.33 | m-vs |
| 21.93-22.84 | 4.05-3.89 | m-vs |
| 24.71-25.35 | 3.60-3.51 | w-m |
| 25.73-26.35 | 3.46-3.38 | m-vs |

TABLE C (UZM-15)

| 2-θ | d(Å) | $I/I_0$ % |
|---|---|---|
| 8.35-9.30 | 10.58-9.50 | w-m |
| 12.30-13.30 | 7.19-6.65 | w-m |
| 16.60-17.20 | 5.34-5.15 | w-m |
| 19.00-19.80 | 4.67-4.48 | w-m |

TABLE C-continued (UZM-15)

| 2-θ | d(Å) | $I/I_0$ % |
|---|---|---|
| 20.80-22.30 | 4.27-3.98 | w |
| 23.55-23.95 | 3.77-3.71 | w-m |
| 24.03-24.47 | 3.70-3.63 | w-m |
| 25.50-26.25 | 3.49-3.39 | vs |
| 48.30-49.10 | 1.88-1.85 | w |

TABLE D (UZM-16)

| 2-θ | d(Å) | $I/I_0$ % |
|---|---|---|
| 3.86-4.22 | 22.87-20.92 | w-m |
| 7.60-7.84 | 11.62-11.27 | s-vs |
| 11.58-11.86 | 7.64-7.46 | w-m |
| 13.29-13.54 | 6.65-6.53 | m |
| 13.90-14.20 | 6.36-6.23 | w |
| 15.34-15.68 | 5.77-5.65 | m |
| 19.30-19.65 | 4.60-4.51 | m |
| 20.37-20.73 | 4.35-4.28 | m-s |
| 23.18-23.54 | 3.83-3.78 | m-s |
| 23.57-23.89 | 3.77-3.72 | s-vs |
| 24.68-25.03 | 3.60-3.55 | m-s |
| 26.84-27.23 | 3.32-3.27 | m |
| 28.15-28.58 | 3.17-3.12 | m |
| 31.25-31.71 | 2.86-2.82 | vs |
| 33.37-33.76 | 2.68-2.65 | w |
| 35.89-36.36 | 2.50-2.47 | m |
| 48.05-48.52 | 1.89-1.87 | w-m |
| 51.38-51.90 | 1.78-1.76 | w-m |
| 55.35-56.04 | 1.66-1.64 | w-m |
| 58.08-58.64 | 1.59-1.57 | w |

The UZM-8, UZM-15 and UZM-16 zeolites are prepared by a hydrothermal crystallization of a reaction mixture prepared by combining reactive sources of R, aluminum, silicon and optionally M and E. The sources of aluminum include but are not limited to aluminum alkoxides, precipitated aluminas, aluminum metal, sodium aluminate, organoammonium aluminates, aluminum salts and alumina sols. Specific examples of aluminum alkoxides include, but are not limited to aluminum ortho sec-butoxide and aluminum ortho isopropoxide. Sources of silica include but are not limited to tetraethylorthosilicate, colloidal silica, precipitated silica, alkali silicates and organoammonium silicates. A special reagent consisting of an organoammonium aluminosilicate solution can also serve as the simultaneous source of Al, Si, and R. Sources of the E elements include but are not limited to alkali borates, boric acid, precipitated gallium oxyhydroxide, gallium sulfate, ferric sulfate, ferric chloride, chromium nitrate and indium chloride. Sources of the M metals include the halide salts, nitrate salts, acetate salts, and hydroxides of the respective alkali or alkaline earth metals. R can be introduced as an organoammonium cation or an amine. When R is a quaternary ammonium cation or a quaternized alkanolammonium cation, the sources include but are not limited to the hydroxide, chloride, bromide, iodide and fluoride compounds. Specific examples include without limitation DEDMA hydroxide, ETMA hydroxide, tetramethylammonium hydroxide, tetraethylammonium hydroxide, hexamethonium bromide, tetrapropylammonium hydroxide, methyltriethylammonium hydroxide, tetramethylammonium chloride, propylethyldimethylammonium hydroxide (PEDMAOH), trimethylpropylammonium hydroxide, trimethylbutylammonium hydroxide (TMBAOH), N,N,N,N',N',N'-hexamethyl 1,4 butanediammonium hydroxide (DQ4), and choline chloride. The source of R may also be neutral amines, diamines, and alkanolamines that subsequently hydrolyzes to form an organoammonium cation. Specific examples are triethanolamine, triethylamine, and N,N,N',N' tetramethyl-1,6-hexanediamine. Preferred sources of R without limitation are ETMAOH, DEDMAOH, and HM(OH)$_2$.

In a special case, a reagent in the form of an aluminosilicate stock solution may be used. These solutions consist of one or more organoammonium hydroxides and sources of silicon and aluminum that are processed to form a clear homogenous solution that is generally stored and used as a reagent. The reagent contains aluminosilicate species that typically don't show up in zeolite reaction mixtures derived directly from separate sources of silicon and aluminum. The reagent is generally alkali-free or contains alkali at impurity levels from the silicon, aluminum, and organoammonium hydroxide sources. One or more of these solutions may be used in a zeolite synthesis. In the case of substitution of Al by E, the corresponding metalosilicate solution may also be employed in a synthesis.

As shown above, not all the R cations can produce all of the three UZM structures. Thus the preparation of UZM-15 requires at least one first organoammonium cation having at least one organic group with at least two carbon atoms, e.g. DEDMA, ETMA, TMBA, DQ4 and PEDMA and optionally (in addition to the first organoammonium cation) a second organoammonium compound. The preparation of UZM-16 requires benzyltrimethylammonium (BzTMA) or a combination of BzTMA and at least one organoammonium cation as described above.

The reaction mixture containing reactive sources of the desired components can be described in terms of molar ratios of the oxides by the formula:

$$aM_{2/n}O:bR_{2/p}O:(1-c)Al_2O_3:cE_2O_3:dSiO_2:eH_2O.$$

The values of the variables for the UZM-8, 15 and 16 are presented in Table E along with general and preferred reaction conditions. The reaction mixtures are reacted at the stated conditions in a sealed reaction vessel under autogenous pressure.

After crystallization is complete, the solid product is isolated from the heterogeneous mixture by means such as filtration or centrifugation, and then washed with de-ionized water and dried in air at ambient temperature up to about 100° C.

As-synthesized, the zeolites will contain some of the exchangeable or charge balancing cations in its pores. These exchangeable cations can be exchanged for other cations, or in the case of organic cations, they can be removed by heating under controlled conditions. Ion exchange involves contacting the zeolites with a solution containing the desired cation (at molar excess) at exchange conditions. Exchange conditions include a temperature of about 15° C. to about 100° C. and a time of about 20 minutes to about 50 hours. Calcination conditions include a temperature of about 300° C. to about 600° C. for a time of about 2 to about 24 hours.

A special treatment for removing organic cations which provides the ammonium form of the zeolite is ammonia calcination. Calcination in an ammonia atmosphere can decompose organic cations, presumably to a proton form that can be neutralized by ammonia to form the ammonium cation. The resulting ammonium form of the zeolite can be further ion-exchanged to any other desired form. Ammonia calcination conditions include treatment in the ammonia atmosphere at temperatures between about 250° C. and about 600° C. and more preferably between about 250° C. and about 450° C. for times of 10 minutes to 5 hours. Optionally, the treatments can be carried out in multiple steps within this temperature range such that the total time in the ammonia atmosphere does not exceed 5 hours. Above 500° C., the treatments should be brief, less than a half hour and more preferably on the order of 5-10 minutes. Extended calcination times above 500° C. can lead to unintended dealumination along with the desired ammonium ion-exchange and are unnecessarily harsh as most organoammonium templates easily decompose at lower temperatures.

The UZM-4M, UZM-5HS, UZM-8HS, UZM-15HS and UZM-16HS zeolites are prepared from their respective parent zeolite by a number of various techniques and are represented by the empirical formula:

$$M1_a^{n+}Al_{(1-x)}E_xSi_yO_{z''} \quad (2).$$

In formula (2), E and "x" are as defined above except for UZM-4M and UZM-5HS where "x" varies from 0 to about 0.5. M1 is at least one exchangeable cation selected from the group consisting of alkali metals, alkaline earth metals, rare

TABLE E

Reaction Mixture Compositions and Reaction Conditions for UZM Zeolites

| Variable | UZM-8 | UZM-15 | UZM-16 |
|---|---|---|---|
| a | 0 to about 25 | 0 to about 5 | 0 to about 5 |
| b | about 1 to about 80 | about 1.5 to about 80 | about 1 to about 120 |
| c | 0 to about 1.0 | 0 to about 1.0 | 0 to about 1.0 |
| d | about 10 to about 100 | about 10 to about 100 | about 5 to about 100 |
| e | about 100 to about 1500 | about 100 to about 1500 | about 50 to about 1500 |
| Temp(° C.)- broad range | about 85° C. to about 225° C. | about 85° C. to about 225° C. | about 80° C. to about 160° C. |
| Temp(° C.)- preferred range | about 125° C. to about 150° C. | about 140° C. to about 175° C. | about 95° C. to about 125° C. |
| Time- broad range | about 1 day to about 28 days | about 12 hrs. to about 20 days | about 2 days to about 30 days |
| Time- preferred range | about 5 days to about 14 days | about 2 days to about 10 days | about 5 days to about 15 days | earth metals, ammonium ion, hydrogen ion and mixtures thereof, a is the mole ratio of M1 to (Al+E), n is the weighted average valence of M1, y' is the mole ratio of Si to (Al+E) and z" is the mole ratio of O to (Al+E). The values of the variables for the zeolites are presented below in Table F.

TABLE F

| Variable | UZM-4M | UZM-5HS | UZM-8HS | UZM-15HS | UZM-16HS |
|---|---|---|---|---|---|
| a | about 0.15 to about 1.5 | about 0.15 to about 50 | about 0.05 to about 50 | about 0.01 to about 50 | about 0.01 to about 50 |
| n | about 1 to about 3 | about 1 to about 3 | about 1 to about 3 | about 1 to about 3 | about 1 to about 3 |
| y' | about 1.75 to about 500 | greater than about 5 | greater than about 6.5 | greater than about 7 | greater than about 3 |
| z" | $(a \cdot n + 3 + 4 \cdot y')/2$ | $(a \cdot n + 3 + 4 \cdot y')/2$ | $(a \cdot n + 3 + 4 \cdot y')/2$ | $(a \cdot n + 3 + 4 \cdot y')/2$ | $(a \cdot n + 3 + 4 \cdot y')/2$ |

The value of y' is greater than the specific value set forth in Table F to virtually pure silica. By virtually pure silica is meant that virtually all the aluminum and/or the E metals have been removed from the framework. It is well know that it is virtually impossible to remove all the aluminum and/or E metal. Numerically, a zeolite is virtually pure silica when y' has a value of at least 3,000, preferably 10,000 and most preferably 20,000. Thus, ranges for y' are from 3, 5, 6.5 or 7 to 3,000 preferably greater than 10 to about 3,000; 3, 5, 6.5 or 7 to 10,000 preferably greater than 10 to about 10,000 and 3, 5, 6.5 or 7 to 20,000 preferably greater than 10 to about 20,000.

The zeolites UZM-4M, UZM-5HS, UZM-8HS, UZM-15HS and UZM-16HS are further characterized by an x-ray diffraction pattern having at least the d-spacings and relative intensities set forth in Tables G, H, I, J and K respectively.

TABLE G

UZM-4M

| $2\theta$ | d(Å) | $I/I_0$ % |
|---|---|---|
| 6.55-6.83 | 13.49-12.93 | m |
| 7.63-7.91 | 11.58-11.17 | vs |
| 13.27-13.65 | 6.67-6.48 | m-s |
| 14.87-15.25 | 5.95-5.81 | m-vs |
| 15.35-15.74 | 5.77-5.63 | m |
| 18.89-19.31 | 4.69-4.59 | m |
| 20.17-20.50 | 4.40-4.33 | w-m |
| 20.43-20.85 | 4.34-4.26 | m |
| 21.51-21.97 | 4.13-4.04 | m-vs |
| 24.14-24.67 | 3.68-3.60 | m-s |
| 24.47-24.98 | 3.63-3.56 | m-s |
| 27.73-28.27 | 3.21-3.15 | w-m |
| 30.11-30.73 | 2.97-2.90 | m-s |
| 31.13-31.75 | 2.87-2.81 | w-m |

TABLE H

UZM-5HS

| $2\theta$ | d(Å) | $I/I_0$ % |
|---|---|---|
| <6.79 | >13.0 | w-m |
| 8.26-7.52 | 10.70-11.75 | m-vs |
| 10.65-10.04 | 8.30-8.80 | m-vs |
| 12.32-11.79 | 7.18-7.50 | s-vs |
| 16.56-15.53 | 5.35-5.70 | m-vs |
| 19.71-18.78 | 4.50-4.72 | w-m |

TABLE H-continued

UZM-5HS

| $2\theta$ | d(Å) | $I/I_0$ % |
|---|---|---|
| 23.58-22.72 | 3.77-3.91 | w-m |
| 24.37-23.64 | 3.65-3.76 | m-vs |

TABLE I

UZM-8HS

| $2\theta$ | d(Å) | $I/I_0$ % |
|---|---|---|
| 6.90-7.40 | 12.8-11.94 | w-vs |
| 8.15-8.85 | 10.84-9.98 | m-vs |
| 14.10-14.70 | 6.28-6.02 | w-vs |
| 19.40-20.10 | 4.57-4.41 | w-s |
| 22.00-22.85 | 4.04-3.89 | m-vs |
| 24.65-25.40 | 3.61-3.50 | w-m |
| 25.70-26.50 | 3.46-3.36 | w-vs |

TABLE J

UZM-15HS

| $2\theta$ | d(Å) | $I/I_0$ % |
|---|---|---|
| 8.75-10.30 | 10.12-8.60 | w-vs |
| 12.70-13.40 | 6.98-6.62 | m-s |
| 19.00-20.30 | 4.68-4.38 | w |
| 25.50-26.50 | 3.50-3.37 | m-vs |

TABLE K

UZM-16HS

| $2\theta$ | d(Å) | $I/I_0$ % |
|---|---|---|
| 7.70-8.40 | 11.47-10.52 | m-vs |
| 11.70-12.10 | 7.56-7.31 | w |
| 13.35-14.56 | 6.63-6.08 | s-vs |
| 20.60-21.70 | 4.31-4.09 | w |
| 24.60-25.65 | 3.62-3.47 | m-s |

The UZM-4M, UZM-5HS, UZM-8HS, 15HS and 16HS are prepared by removing aluminum and optionally inserting silicon into the structure thereby increasing the Si/Al ratio and thus modifying the acidity and ion exchange properties of the zeolites. These treatments include: a) contacting with a fluorosilicate solution or slurry; b) calcining or steaming followed by acid extraction or ion-exchange; c) acid extraction or d) any combination of these treatments in any order.

Fluorosilicate treatment is known in the art and is described in U.S. Pat. No. 6,200,463 B1, which cites U.S. Pat. No. 4,711,770 as describing a process for treating a zeolite with a fluorosilicate salt. Both patents are incorporated by reference in their entirety. General conditions for this treatment are contacting the zeolite with a solution containing a fluorosilicate salt such as ammonium fluorosilicate (AFS) at a temperature of about 20° C. to about 90° C.

The acids which can be used in carrying out acid extraction include without limitation mineral acids, carboxylic acids and mixtures thereof. Examples of these include sulfuric acid, nitric acid, ethylenediaminetetraacetic acid (EDTA), citric acid, oxalic acid, etc. The concentration of acid which can be used is not critical but is conveniently between about 1 wt. % to about 80 wt. % acid and preferably between 5 wt. % and 40 wt. % acid. Acid extraction conditions include a temperature of about 10° C. to about 100° C. for a time of about 10 minutes to about 24 hours. Once treated with the acid, the treated UZM zeolite is isolated by means such as filtration, washed with deionized water and dried at ambient temperature up to about 100° C.

The extent of dealumination obtained from acid extraction depends on the cation form of the starting UZM as well as the acid concentration and the time and temperature over which the extraction is conducted. For example, if organic cations are present in the starting UZM zeolite, the extent of dealumination will be slight compared to a UZM zeolite in which the organic cations have been removed. This may be preferred if it is desired to have dealumination just at the surface of the UZM zeolite. As stated above, convenient ways of removing the organic cations include calcination, ammonia calcination, steaming and ion exchange. Calcination, ammonia calcination and ion exchange conditions are as set forth above. Steaming conditions include a temperature of about 400° C. to about 850° C. with from about 1% to about 100% steam for a time of about 10 minutes to about 48 hours and preferably a temperature of about 500° C. to about 600° C., steam concentration of about 5 to about 50% and a time of about 1 to about 2 hours.

It should be pointed out that both calcination and steaming treatments not only remove organic cations, but can also dealuminate the zeolite. Thus, alternate embodiments for dealumination include: a calcination treatment followed by acid extraction and steaming followed by acid extraction. A further embodiment for dealumination comprises calcining or steaming the starting UZM zeolite followed by an ion-exchange treatment. Of course an acid extraction can be carried out concurrently with, before or after the ion exchange.

The ion exchange conditions are the same as set forth above, namely a temperature of about 15° C. to about 100° C. and a time of about 20 minutes to about 50 hours. Ion exchange can be carried out with a solution comprising a cation (M1') selected from the group consisting of alkali metals, alkaline earth metals, rare earth metals, hydrogen ion, ammonium ion, and mixtures thereof. By carrying out this ion exchange, the M1 cation is exchanged for a secondary or different M1' cation. In a preferred embodiment, the UZM composition after the steaming or calcining steps is contacted with an ion exchange solution comprising an ammonium salt. Examples of ammonium salts include but are not limited to ammonium nitrate, ammonium chloride, ammonium bromide, and ammonium acetate. The ammonium ion containing solution can optionally contain a mineral acid such as but not limited to nitric, hydrochloric, sulfuric and mixtures thereof. The concentration of the mineral acid is that amount necessary to give a ratio of $H^+$ to $NH_4^+$ of 0 to 1. This ammonium ion exchange aids in removing any debris present in the pores after the steaming and/or calcination treatments.

It is apparent from the foregoing that, with respect to effective process conditions, it is desirable that the integrity of the zeolite crystal structure be substantially maintained throughout the dealumination process, and that the zeolite retains at least 50%, preferably at least 70% and more preferably at least 90% of its original crystallinity. A convenient technique for assessing the crystallinity of the products relative to the crystallinity of the starting material is the comparison of the relative intensities of the d-spacing of their respective X-ray powder diffraction patterns. The sum of the peak intensities, in arbitrary units above the background, of the starting material is used as the standard and is compared with the corresponding peak intensities of the products. When, for example, the numerical sum of the peak heights of the molecular sieve product is 85 percent of the value of the sum of the peak intensities of the starting zeolite, then 85 percent of the crystallinity has been retained. In practice it is common to utilize only a portion of the peaks for this purpose, as for example, five or six of the strongest peaks. Other indications of the retention of crystallinity are surface area and adsorption capacity. These tests may be preferred when the substituted metal significantly changes, e.g., increases, the absorption of x-rays by the sample or when peaks experience substantial shifts such as in the dealumination process.

After having undergone any of the dealumination treatments as described above, the UZM zeolite is usually dried and can be used as discussed below. The properties of the modified UZM zeolite can be further modified by one or more additional treatment. These treatments include steaming, calcining or ion exchanging and can be carried out individually or in any combination. Some of these combinations include but are not limited to:

steam ⟶ calcine ⟶ ion exchange;
calcine ⟶ steam ⟶ ion exchange;
ion exchange ⟶ calcine ⟶ steam
ion exchange ⟶ steam ⟶ calcine;
steam ⟶ calcine;

The dealumination treatment described above can be combined in any order to provide the zeolites of the invention although not necessarily with equivalent result. It should be pointed out that the particular sequence of treatments, e.g., AFS, acid extraction, steaming, calcining, etc can be repeated as many times as necessary to obtain the desired properties. Of course one treatment can be repeated while not repeating other treatments, e.g., repeating the AFS two or more times before carrying out steaming or calcining, etc. Finally, the sequence and/or repetition of treatments will determine the properties of the final UZM-4M, UZM-5HS, UZM-8HS, 15HS or 16HS composition.

In specifying the proportions of the zeolite starting material or adsorption properties of the zeolite product and the like herein, the "anhydrous state" of the zeolite will be intended unless otherwise stated. The term "anhydrous state" is employed herein to refer to a zeolite substantially devoid of both physically adsorbed and chemically adsorbed water.

A second component of the catalyst of the invention is a catalytic metal component which is selected from the metals of Group VIII (Groups 8, 9 and 10 of the IUPAC designation) of the Periodic Table of the Elements and preferably from the noble metals. The group of noble metals are ruthenium, rhodium, palladium, platinum, iridium osmium. Preferred catalytic metals are platinum, palladium, rhodium, ruthenium, iridium and mixtures thereof.

The catalytic metal component can be deposited either on the molecular sieve or on a refractory inorganic oxide component. Inorganic oxides which can be used are any of those well known in the art and include but are not limited to aluminas, silica/alumina, silica, titania, calcium oxide, magnesium oxide, clays and zirconia. In order to avoid confusion it is pointed out that the term silica/alumina does not mean a physical mixture of silica and alumina but means an acidic and amorphous material that has been cogelled or coprecipitated. The term is well known in the art, see e.g. U.S. Pat. Nos. 3,909,450; 3,274,124 and 4,988,659. The aluminas which can be used include gamma alumina, theta alumina, delta and alpha alumina.

The catalytic metal component is deposited onto either the zeolite or inorganic oxide by means well known in the art such as spray impregnation or evaporative impregnation. Both spray or evaporative impregnation use a solution containing a decomposable compound of the desired metal. By decomposable is meant that upon heating the compound decomposes to provide the catalytic metal or catalytic metal oxide. Non-limiting examples of decomposable compounds which can be used include chloroplatinic acid, palladic acid, chloroiridic acid, rhodium trichloride, ruthenium tetrachloride, osmium trichloride, iron chloride, cobalt chloride, nickel chloride, iron nitrate, cobalt nitrate, nickel nitrate, rhodium nitrate, ammonium chloroplatinate, platinum tetrachloride hydrate, palladium chloride, palladium nitrate, tetraamine platinum chloride and tetraamminepalladium (II) chloride. The solvent which is used to prepare the solution is usually water although organic solvents such as alcohols, dimethyl formamide (DMF), dimethylsulfoxide (DMSO), tetrahydrofuran (THF) and amines, e.g., pyridine can be used.

Spray impregnation involves taking a small volume of the solution and spraying it over the support (zeolite or oxide) while the support is moving. When the spraying is over, the wetted support can be transferred to other apparatus for drying or finishing steps.

One particular method of evaporative impregnation involves the use of a steam-jacketed rotary dryer. In this method the support is immersed in the impregnating solution which has been placed in the dryer and the support is tumbled by the rotating motion of the dryer. Evaporation of the solution in contact with the tumbling support is expedited by applying steam to the dryer jacket. The impregnated support is then dried at a temperature of about 60° C. to about 300° C. and then calcined at a temperature of about 300° C. to about 850° C. for a time of about 30 minutes to about 8 hours to give the calcined catalyst.

When the zeolite is the support, the catalytic metal component can also be deposited thereon by ion-exchange. Ion-exchange is carried out by contacting the zeolite with a solution containing a compound of the desired metal at ion-exchange conditions which include a temperature of about 20° C. to about 100° C. for a time from about 5 minutes to about 6 hours.

When the catalytic metal component is deposited on the refractory inorganic oxide component, the catalyst comprises separate particles. One configuration is a loose mixture of the two particles (refractory oxide and zeolite particles) or the particles are mixed and then formed into shaped articles such as cylinders, pellets, pills, spheres, irregularly shaped particles, etc. Methods of preparing such shaped articles are well known in the art. In the case where the catalytic metal is deposited on the zeolite, then the inorganic oxide acts as a binder so that the resultant mixture can be formed into any of the shapes described above.

In another embodiment, the zeolite and inorganic oxide are first mixed and formed into a shaped article and then the catalytic metal is deposited onto the composite article by any of the means described above. In this case, the catalytic metal is believed to be deposited on both the inorganic oxide and zeolite supports. Regardless of how and where the catalytic metal is deposited, it is present in the final catalyst in an amount from about 0.01 to about 10 weight percent of the catalyst expressed as the metal. It should also be pointed out that the metal component can be present on the catalyst in its elemental (zero valent) state or as the oxide.

The catalyst also contains a modifier which modifies the activity of the catalytic metal. The modifier is selected from the group consisting of titanium, niobium, rare earth elements, tin, rhenium, zinc, germanium and mixtures thereof. Preferred rare earth elements are cerium, ytterbium, lanthanum, dysprosium and mixtures thereof. The modifier component is deposited by the same techniques as described above for the catalytic metals. Further, the modifier can be deposited on the support before, after or simultaneously with the catalytic metal, although not necessarily with equivalent results. It is preferred to deposit the modifier with the catalytic metal. The amount of modifier can vary substantially but is usually in the range of about 0.1 to about 50 wt. %, preferably about 1 to about 10 wt. % of the catalyst as the element.

The catalyst described above is used in a process where cyclic paraffins are opened or cleaved to acyclic paraffins. The feeds which can be used in the ring opening process are any of those which comprises $C_5$-$C_6$ aliphatic rings, i.e. naphthenic rings. Naphtha feeds can vary considerably in the amount of aromatic, naphthene and paraffin components which they complain. One example of naphtha feed was found to contain about 17 wt. % aromatics, 44 wt. % naphthenes and 39 wt. % aromatics.

The feedstream is contacted with the catalyst at ring opening conditions which include a temperature of about 200° C. to about 600° C., a pressure of about atmospheric to about 20,684 kPag, (3000 psig) and preferably from about 1379 kPag (200 psig) to about 13790 kPa (2000 psig), a liquid hourly space velocity of about 0.1 to about 30 $hr^{-1}$ and preferably about 2 to about 10 $hr^{-1}$ and $H_2$/HC (hydrocarbon) ratio from about 0.1 to about 30 and preferably from about 1 to about 10.

The following examples are presented in illustration of this invention and are not intended as undue limitations on the generally broad scope of the invention as set out in the appended claims.

EXAMPLE 1

An aluminum sol was prepared by dissolving aluminum metal in HCl. In a container 822.4 g of the Al-sol, containing 105.32 g Al (as $Al_2O_3$) and 94 g Cl were blended with 2.91 g of $NbCl_5$ at 60° C. for 12 hours. To this there were added 302.1 g of hexamethylene tetraamine (HMT) and 15.4 g of water. Droplets of the resulting mixture were formed and dropped into a hot oil tower which formed gelled spheres. The spheres were then aged at 140° C. for 1.5 hours, washed with 20 liters of 0.25% $NH_3$ solution for 2 hours at 95° C., dried at 100° C. for 16 hours and then calcined at 550° C. for 2 hours in air with 3% steam.

In a rotary impregnator, 50 cc of the above spheres were impregnated with a 50 cc aqueous solution containing 8.89 cc of chloroplatinic acid (CPA) (Pt concentration was 28.08 mg Pt/cc) and 2 g of HCl (37%). The excess solution was evaporated at 100° C. and the catalyst was then calcined at 525° C. in flowing air (3600 cc/min.) and 45 cc/min. of 1.0M HCl for 30 minutes. Finally, the calcined catalyst was reduced at 500° C. with 3000 cc/min. of $H_2$ for one hour. Analysis of the catalyst showed it contained 0.93 wt. % Pt and 0.49 wt. % Nb. This catalyst was identified as catalyst A.

EXAMPLE 2

In a container 766.2 g of alumina was mixed with 27 g $HNO_3$ (70%) followed by the addition of 71.4 g $TiO_2$ and 563.9 g of water and mixed for 30 minutes to form a dough. The dough was extruded through a 0.073" dieplate and the extrudates calcined in air at 550° C. for two hours.

In a rotary evaporator, 72.26 g of the above extrudates were combined with 100 ml of an aqueous solution containing 4.92 ml of HCl (37%) and 12.8 ml of CPA. The solution was evaporated and the catalyst was calcined and then reduced as described in Example 1. Analysis of the catalyst showed it contained 0.49 wt. % Pt. This catalyst was identified as catalyst B.

EXAMPLE 3

In a rotary evaporator 148.24 g of gamma alumina extrudates were impregnated with 200 ml of an aqueous solution containing 26.03 mL of CPA, 1.60 g $La(NO_3)_3$ and 9.99 mL HCl (44%). The wet powder was dried, calcined and reduced as described in Example 1. Analysis of the catalyst showed it contained 0.5 wt. % Pt and 0.32 wt. % La. This catalyst was identified as catalyst C.

EXAMPLE 4

In a rotary evaporator 148.24 g of gamma alumina extrudates were impregnated with 200 mL of an aqueous solution containing 26.68 mL of CPA, 1.11 g of $NbCl_5$ and 9.99 mL HCl (44%). The wet extrudates were dried, calcined and reduced as described in Example 1. Analysis of the catalyst showed it contained 0.48 wt. % Pt and 0.16 wt. % Nb. This catalyst was identified as catalyst D.

EXAMPLE 5

In a rotary evaporator 63.63 g of theta alumina oil dropped spheres were impregnated with 100 mL of an aqueous solution containing 11.45 mL of CPA, 0.62 g of $YbCl_3..6H_2O$ and 4.29 mL HCl (44%). The wet spheres were dried, calcined and reduced as described in Example 1. Analysis of the catalyst showed it contained 0.49 wt. % Pt and 0.46 wt. % Yb. This catalyst was identified as catalyst E.

EXAMPLE 6

In a rotary evaporator 148.24 g of gamma alumina extrudates were impregnated with 200 mL of an aqueous solution containing 26.68 mL of CPA, and 9.99 mL HCl (44%). The wet extrudates were dried, calcined and reduced as described in Example 1. Analysis of the catalyst showed it contained 0.52 wt. % Pt. This catalyst was identified as catalyst F.

EXAMPLE 7

In a rotary evaporator 148.28 g of gamma alumina extrudates were impregnated with 200 mL of an aqueous solution containing 26.68 mL of CPA, 1.45 g $YbCl_3..6H_2O$ and 9.99 mL HCl (44%). The wet extrudates were dried, calcined and reduced as described in Example 1. Analysis of the catalyst showed it contained 0.51 wt. % Pt and 0.40 wt. % Yb. This catalyst was identified as catalyst G.

EXAMPLE 8

In a rotary evaporator 95.73 g of theta alumina oil dropped spheres were impregnated with 150 mL of an aqueous solution containing 17.41 mL of CPA and 6.52 mL HCl (44%). The wet spheres were dried, calcined and reduced as described in Example 1. Analysis of the catalyst showed it contained 0.50 wt. % Pt. This catalyst was identified as catalyst H.

EXAMPLE 9

In a rotary evaporator 148.24 g of alumina extrudates were impregnated with an aqueous solution containing 200 mL of CPA, 1.62 g $Dy(NO_3)_3$ and 9.99 mL HCl (44%). The wet extrudates were dried, calcined and reduced as described in Example 1. Analysis of the catalyst showed it contained 0.50 wt. % Pt and 0.39 wt. % Dy. This catalyst was identified as catalyst I.

EXAMPLE 10

Catalysts B to I were tested for methylcyclopentane ring opening activity and selectivity as follows. The catalysts were tested by placing 35 mg of 250-450 um meshed particles into a microreactor and pretreated at 450° C. for 4 hours using dry hydrogen floured at 45 $cm^3$/min. The samples were then tested using a feed of 2.7% methylcyclopentane in hydrogen as a carrier gas at temperatures of 200° C. to 350° C. at weight hourly space velocities (w 2/sv) of 0.5 to 6 $hr^{-1}$. The results of the testing at 350° C. and WHSV of 0.5 $hr^{-1}$ are presented in Table 1.

TABLE 1

| Effect of Modifiers on Ring Opening Activity | | |
|---|---|---|
| Catalyst I.D. | MCP Conv. % | RO Yield % |
| B | 80 | 72 |
| C | 74 | 71 |
| D | 82 | 75 |
| E | 73 | 70 |
| F | 68 | 60 |
| G | 65 | 60 |
| H | 62 | 57 |
| I | 59 | 55 |

The results provided in Example 10 show that modifiers such as Nb, Ti, and Yb improve both the activity and selectivity of platinum for ring opening.

EXAMPLE 11

Samples of catalysts A, B and H were mixed with a sample of UZM-16 (70% UZM-16/30% catalyst) and tested for methylcyclohexane ring opening activity and selectivity as follows. In an Incollog 800 H™ tube reactor there were placed 2.0 g of 40-60 mesh crushed extrudates of A, B or H and 1.0 g of UZM-16. The reactor was heated using an infrared furnace. Inert spacers were placed before the catalyst bed to minimize dead volume and pre-heat the feed. The feed consisted of methylcyclohexane (>98% purity) which was mixed with hydrogen carrier gas (>99% pure) in a heated mixing chamber and then downflowed through the catalyst bed at a weight hourly space velocity of 1.5 hr$^{-1}$. Measurements were taken at temperatures of 260-400° C. and a pressure of 5516 kPag (800 psig). The reactor effluent was analyzed by an on-line gas chromatograph and the results are presented in Table 2.

TABLE 2

Effect of Molecular Sieves on Ring Opening Activity

| Catalyst ID | Temperatures | MCH Conversion (wt. %) | $C_7$ Paraffin Select. (wt. %) | $C_7$ Paraffin Yield % |
|---|---|---|---|---|
| UZM-16 + Cat H | 383 | 86 | 52 | 45 |
| UZM-16 + Cat A | 391 | 93 | 59 | 55 |
| UZM-16 + Cat B | 401 | 96 | 54 | 52 |

What is claimed is:

1. A catalyst for opening cyclic paraffins comprising a Group VIII (IUPAC Groups 8-10) metal component, a modifier component, a molecular sieve and a refractory inorganic oxide, the molecular sieve characterized in that it has an OH peak shift in its CO-FTIR spectrum of less than 310 cm$^{-1}$ and is selected from the group consisting of UZM-4, UZM-4M, UZM-5, UZM-5HS, UZM-5P, UZM-6, UZM-8, UZM-8HS, UZM-15, UZM-15HS, UZM-16, UZM-16HS and mixtures thereof.

2. The catalyst of claim 1 where the Group VIII metal is selected from the group consisting of platinum, palladium, rhodium, ruthenium, iridium and mixtures thereof.

3. The catalyst of claim 1 where the catalyst is a physical mixture of molecular sieve particles and refractory inorganic oxide particles.

4. The catalyst of claim 1 where the Group VIII metal component is deposited on the molecular sieve.

5. The catalyst of claim 1 where the Group VIII metal component is deposited on the refractory inorganic oxide.

6. The catalyst of claim 1 where the refractory inorganic oxide is selected from the group consisting of alumina, silica, silica/alumina, calcium oxide, magnesium oxide, clays, zirconia and mixtures thereof.

7. The catalyst of claim 1 where the catalyst is formed into a shaped article selected from the group consisting of pills, extrudates, spheres, irregularly shaped particles and tablets.

8. The catalyst of claim 1 where the Group VIII metal component is present in an amount from about 0.01 to about 10 wt. % of the catalyst as the metal.

9. The catalyst of claim 1 where the modifier component is selected from the group consisting of titanium, niobium, rare earth elements, tin, rhenium, zinc, germanium and mixtures thereof.

10. The catalyst of claim 9 where the modifier component is present in an amount from about 0.1 to about 50 wt. % of the catalyst as the element.

11. The catalyst of claim 9 where the rare earth element is selected from the group consisting of cerium, ytterbium, lanthanum, dysprosium and mixtures thereof.

12. The catalyst of claim 1 where the molecular sieve is selected from those having 8, 10 or 12 ring pores and having weak to medium acidity.

* * * * *